(12) United States Patent
MacLean

(10) Patent No.: US 8,449,499 B2
(45) Date of Patent: May 28, 2013

(54) SPRING DRIVEN ADJUSTABLE ORAL SYRINGE

(75) Inventor: Rebecca MacLean, Castle Rock, CO (US)

(73) Assignee: Maclean, LLC, Castle Rock, CO (US)

( * ) Notice: Subject to any disclaimer, the term of this patent is extended or adjusted under 35 U.S.C. 154(b) by 0 days.

(21) Appl. No.: 13/280,159

(22) Filed: Oct. 24, 2011

(65) Prior Publication Data

US 2012/0101477 A1     Apr. 26, 2012

Related U.S. Application Data

(62) Division of application No. 12/350,001, filed on Jan. 7, 2009, now Pat. No. 8,062,254.

(60) Provisional application No. 61/010,481, filed on Jan. 8, 2008.

(51) Int. Cl.
    *A61M 5/20*          (2006.01)

(52) U.S. Cl.
    USPC ............................................................ 604/135

(58) Field of Classification Search
    USPC ............................................................ 604/135
    See application file for complete search history.

(56) References Cited

U.S. PATENT DOCUMENTS

| | | | |
|---|---|---|---|
| 4,030,498 A | 6/1977 | Tompkins | |
| 4,047,527 A | 9/1977 | Kelsen | |
| 4,068,662 A | 1/1978 | Sneider | |
| 4,127,126 A | 11/1978 | Schunk | |
| 4,230,112 A | 10/1980 | Smith | |
| 4,246,898 A | 1/1981 | Travalent et al. | |
| 4,303,070 A | 12/1981 | Ichikawa et al. | |
| 4,303,071 A | 12/1981 | Smith | |
| 4,317,448 A | 3/1982 | Smith | |
| 4,468,223 A | 8/1984 | Minagawa et al. | |
| 4,493,348 A | 1/1985 | Lemmons | |
| 4,526,303 A | 7/1985 | Harrod | |
| 4,581,013 A | 4/1986 | Allen | |
| 4,624,945 A | 11/1986 | Eckenhoff et al. | |
| 4,663,148 A | 5/1987 | Eckenhoff et al. | |
| 4,663,149 A | 5/1987 | Eckenhoff et al. | |
| 4,692,336 A | 9/1987 | Eckenhoff et al. | |
| 4,693,709 A | 9/1987 | Georae et al. | |
| 4,716,031 A | 12/1987 | Eckenhoff et al. | |
| 4,747,838 A | 5/1988 | Wolff et al. | |

(Continued)

OTHER PUBLICATIONS

"Does a Color-Coded Method for Measuring Acetaminophen Doses Reduce the Likelihood of Dosing Error?" Arch. Pediatr. Adolesc Med., 2004; 158: 625-627, pp. 26-30.

(Continued)

*Primary Examiner* — Jason Flick
(74) *Attorney, Agent, or Firm* — Sheridan Ross PC

(57) ABSTRACT

Embodiments disclosed herein generally describe a medication delivery system. The medication delivery system includes a barrel, a plunger assembly, a dosage selection device, and a force producing element. The plunger assembly is disposed within the barrel. The force producing element can force the plunger assembly from the barrel. The user can select one or two or more dosages with a dosage selection device. The user selects the dosage; then the medication delivery system delivers the same dosage repeatedly. Further, with the force producing element, the user need only depress the plunger assembly into the barrel and does not need to extract the plunger assembly. This allows the user to use only one hand with the medication delivery system.

4 Claims, 8 Drawing Sheets

U.S. PATENT DOCUMENTS

| | | |
|---|---|---|
| 4,753,638 A | 6/1988 | Peters |
| 4,784,641 A | 11/1988 | White |
| 4,804,371 A | 2/1989 | Vaillancourt |
| 4,911,694 A | 3/1990 | Dolan |
| 4,915,697 A | 4/1990 | DuPont |
| 4,927,416 A | 5/1990 | Tomkiel |
| 4,927,633 A | 5/1990 | Eckenhoff et al. |
| 4,943,281 A | 7/1990 | Kothe |
| 5,017,187 A | 5/1991 | Sullivan |
| 5,037,399 A | 8/1991 | Reichert et al. |
| 5,119,560 A | 6/1992 | Noble |
| 5,119,971 A | 6/1992 | Reyman |
| 5,188,610 A | 2/1993 | Rains |
| 5,219,338 A | 6/1993 | Haworth |
| 5,376,081 A | 12/1994 | Sapienza |
| 5,377,879 A | 1/1995 | Isaacs |
| 5,419,773 A | 5/1995 | Rupp |
| 5,425,528 A | 6/1995 | Rains et al. |
| 5,431,680 A | 7/1995 | Jones |
| 5,487,750 A | 1/1996 | Burchett et al. |
| 5,512,047 A | 4/1996 | Dvorak |
| 5,527,297 A | 6/1996 | Paul |
| 5,554,116 A | 9/1996 | Fu-Hsiang |
| 5,733,258 A | 3/1998 | Lane |
| 5,824,012 A | 10/1998 | Burchett et al. |
| 6,132,416 A | 10/2000 | Broselow |
| 6,152,897 A | 11/2000 | Limrell et al. |
| 6,200,295 B1 | 3/2001 | Burchett et al. |
| 6,273,152 B1* | 8/2001 | Buehler et al. .................. 141/22 |
| 6,358,237 B1 | 3/2002 | Paukovits et al. |
| 6,454,788 B1 | 9/2002 | Ashton |
| 6,475,193 B1* | 11/2002 | Park .............................. 604/191 |
| 6,537,244 B2 | 3/2003 | Paukovits et al. |
| 6,612,469 B2 | 9/2003 | Lopez Pardo |
| 6,752,779 B2 | 6/2004 | Paukovits et al. |
| 6,764,469 B2 | 7/2004 | Broselow |
| 6,830,564 B2 | 12/2004 | Gray |
| 6,866,039 B1 | 3/2005 | Wright et al. |
| 6,964,356 B2 | 11/2005 | Kim |
| 7,018,356 B2 | 3/2006 | Wise et al. |
| 7,029,455 B2 | 4/2006 | Flaherty |
| 7,077,826 B1 | 7/2006 | Grav |
| 7,172,085 B2 | 2/2007 | Beaudette |
| 7,175,609 B1 | 2/2007 | Grav |
| 8,062,254 B2 | 11/2011 | MacLean |
| 2003/0097115 A1 | 5/2003 | Gruenberg |
| 2008/0255513 A1* | 10/2008 | Kaal et al. ..................... 604/110 |
| 2009/0076450 A1 | 3/2009 | Caizza et al. |

OTHER PUBLICATIONS

Frush, Karen S. et al., "Evaluation of a Method to Reduce Over-the-Counter Medication Dosing Error," Arch Pediatr Adolesc. Med., 2004; 158: 620-624, pp. 15-25.

Simon, H.K. et al., "Over-the-Counter Medications. Do Parents Give what They Intend to Give?" Arch. Pediatr. Adolesc Med., Jul. 1997; 151, No. 7, pp. 12-14.

Official Action for U.S. Appl. No. 12/350,001, mailed Oct. 6, 2010 7 pages Restriction Requirement.

Official Action for U.S. Appl. No. 12/350,001, mailed Dec. 22, 2010 10 pages.

Notice of Allowance for U.S. Appl. No. 12/350,001, mailed Sep. 1, 2011 10 pages.

* cited by examiner

SPRING DRIVEN ADJUSTABLE ORAL SYRINGE

CROSS REFERENCE TO RELATED APPLICATIONS

This application is a Divisional of U.S. application Ser. No. 12/350,001, filed Jan. 7, 2009 which said application claims the benefit of priority to U.S. Provisional Application No. 61/010,481 filed Jan. 8, 2008, the entire disclosure of each of which are hereby incorporated herein by reference.

FIELD OF THE INVENTION

Medical devices and, more specifically, medicine measuring devices.

BACKGROUND

Parents and caregivers generally have four types of devices to measure out and dispense liquid medication including a manual syringe with a graduated scale printed on the barrel, a "spoon" that is a test tube shape with a spout to drink from, again with a graduated scale on the side, a bulb-type suction syringe with a graduated scale on the barrel, and a cup with graduated scale. These devices require utilizing an often hard to see and difficult to read graduated scale to determine how much medicine is being taken or poured into the device and therefore administered. Caregivers, trying to get just the right amount, often end up pouring medicine back into the medicine bottle, contaminating the medicine. The FDA has sighted overdose of cough and cold medications, especially in very young children, as a common hazard.

BRIEF SUMMARY

Embodiments disclosed herein would alleviate the potential hazard of overdosing liquid medication by having a large, easy to read, color coded display stating the dosage. The user can determine the amount before taking up the liquid. This novel apparatus allows the user to confidently administer a dosage easily and accurately without grappling with the small print of the graduated scale. It would also, utilizing a spring, take in the exact amount of liquid, alleviating the issue of contamination of the medicine in the bottle, and allow the user to draw in the liquid with one hand. In embodiments, the labeling on the device has multiple visual clues as to the chosen dosage so that not only does the window display the written amount, but each different amount has a color coded bar whose length is proportional to the dosage amount, therefore alleviating many typical errors in reading the closing device.

BRIEF DESCRIPTION OF THE DRAWINGS

The embodiments of the present disclosure are described in conjunction with the appended figures.

Figures 1A, 1B:
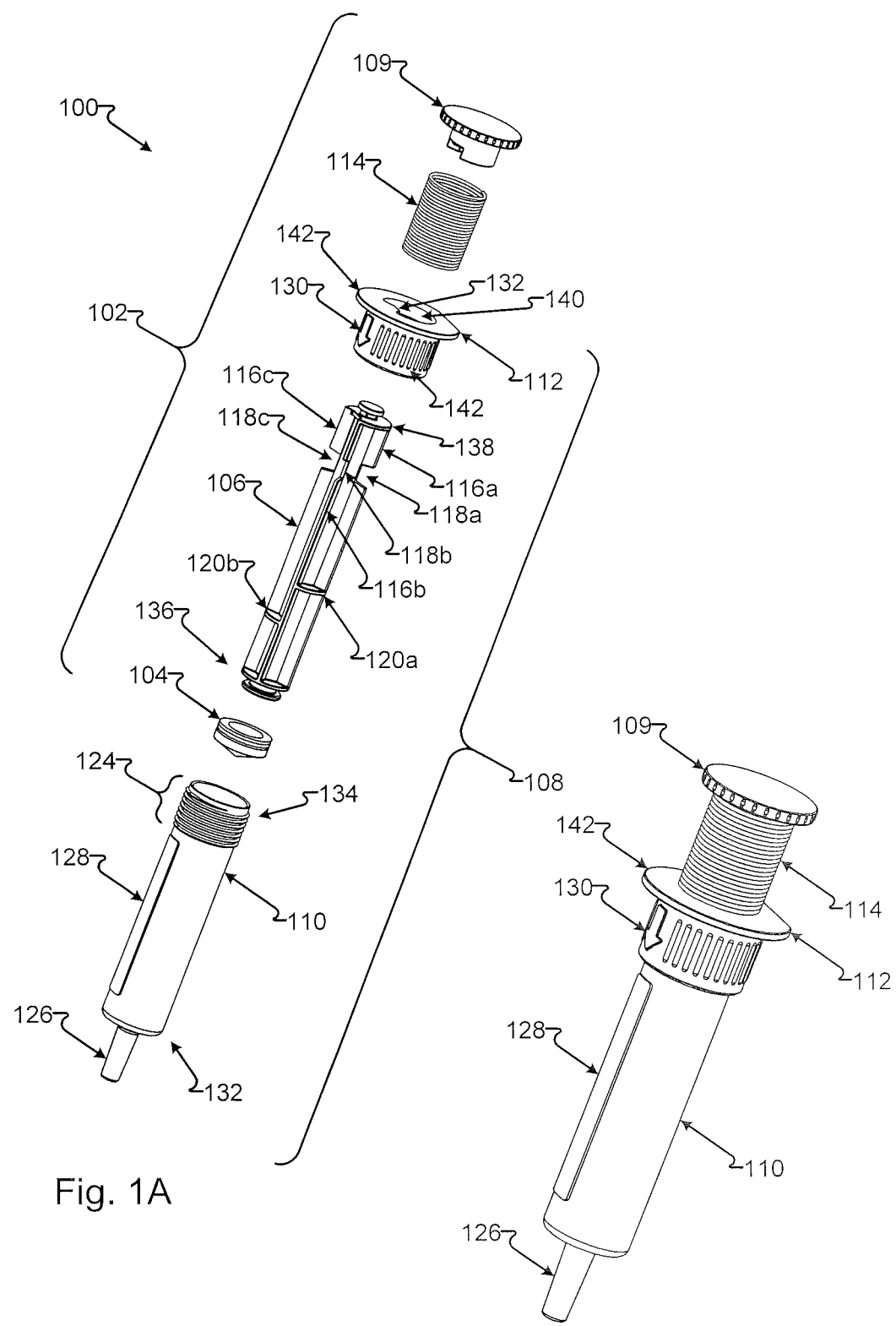
FIG. 1A is an exploded isometric view of an embodiment of a medication delivery system.
FIG. 1B is an isometric view of an embodiment of a medication delivery system.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides exemplary embodiment(s) only and is not intended to limit the scope, applicability or configuration of the possible embodiments. Rather, the ensuing description of the exemplary embodiment(s) will provide those skilled in the art with an enabling description for implementing an exemplary embodiment. It should be understood that various changes may be made in the function and arrangement of elements without departing from the spirit and scope of the possible embodiments as set forth in the appended claims.

Embodiments presented herein provide for a medication delivery device. The medication delivery device can be a syringe allowing a user to select a dosage from several dosages. The dosage is presented to the user in visual form on the syringe. Once selected, the syringe provides the selected dosage. In further embodiments, the syringe also includes a spring that creates a force on the plunger of the syringe. The applied force can cause the syringe to return to an initial position. Thus, the user need only push the plunger into the barrel of the syringe. Thus, the user need only use one hand to operate the syringe, and the syringe can repeatedly administer the same dose without further effort by the user.

A medication delivery system 100 is shown in FIGS. 1 and 2A-2E. The medication delivery system 100 can include a barrel assembly 108 and a plunger assembly 102. The medication delivery system 100 can also include a dosage selection device that can be coupled to or incorporated into the barrel assembly 108 and/or the plunger assembly 102. The dosage selection device can allow the user to select one of two or more dosages for delivery of a medication or liquid. Several embodiments of the medication delivery system 100 are possible, and one embodiment of the medication delivery system is shown in FIGS. 1 and 2A-2E.

The medication delivery system 100, in embodiments, is a syringe as shown in FIGS. 1 and 2A-2E. The medication delivery system 100 may hereinafter be referred to as a syringe. However, the various embodiments are not limited to just syringes or the embodiments shown in the figures as one skilled in the art will see other possible embodiments. The barrel assembly 108 can comprise a barrel 110. The barrel assembly 108 may be formed from a rigid material, for example, a plastic, metal, glass, or other material.

The barrel 110 can include a distal end 132 and a proximal end 134. At the distal end 132 of the barrel 110, a nozzle 126 can be formed into the barrel 110 and an orifice may be formed in the end of the nozzle 126. In embodiments, the barrel assembly 108 also includes a barrel cap 112. The barrel cap 112 can have a detent 132 formed into the barrel cap 112. Further, the barrel cap 112 can include a hole 140 that allows the plunger assembly 102 to pass through the barrel cap 112. The barrel cap 112 can be attached to the proximal end 134 of the barrel 110 after the final assembly. To attach the barrel cap 112, the barrel cap 112 can be screwed onto threads 124 formed in the proximal end 134 of the barrel 110. In other embodiments, the barrel cap 112 may be adhered or mechanically fastened to the barrel 110 through other means. The barrel cap 112 can include a flange 142 formed circumferentially around an end of the barrel cap 112. Further, the barrel cap 112 can include a detent 132 formed within the opening 140 of the barrel cap 112. In embodiments, the barrel cap 112 may also include a visual indicator 130 that directs the user's attention to a dosage marking, as explained in conjunction with FIGS. 2A-2E. The barrel cap 112 can also have ribs 142 formed around the exterior wall of the barrel cap 112. The ribs 142 provide a textured surface for the user to more easily grab.

The plunger assembly 102, which may also be referred to as a piston, can include a shaft 106, a plunger 104, and a plunger cap 109. The shaft 106 and plunger cap 109 may be formed from a rigid material, for example, a plastic, metal, or glass. The plunger 104 may be coupled to or attached to the distal end 136 of the shaft 106. The plunger cap 109 can be coupled to or attached to the proximal end 138 of the shaft 106. After assembly, the plunger assembly 102 may be, at least partially, disposed within the barrel 110. In embodiments, the plunger 104 may be formed from a semi-rigid material, for example, a rubber material. The plunger 104 may be formed as to contact the inner walls of the barrel as the plunger assembly 102 is moved within the barrel 110. The plunger 104 may be formed so as to create an airtight seal within the barrel 110 allowing the syringe 100 to create a vacuum. The vacuum allows the medication delivery system 100 to siphon medication from a bottle or other receptacle as the plunger assembly 102 is pulled from the barrel 110.

The shaft 106 can have two or more lengthwise ribs 116a, 116b, and/or 116c formed along the longitudinal axis of the shaft 106. One or more radial ribs 120a and/or 120b may be formed between the two or more lengthwise ribs 116a, 116b, and/or 116c. Each radial rib 120a and/or 120b may be formed at a predetermined location along the longitudinal axis of the shaft 106 between the distal end 136 and the proximal end 138 of the shaft 106. The predetermined location is determined by the amount of dosage to be siphoned into the barrel when the plunger assembly 102 is pulled from the barrel. The medication delivery system 100 can siphon a predetermined volume of medicine into the barrel 110 by pulling plunger 104 from the distal end of the barrel. When the plunger assembly 102 reaches a predetermined distance from the distal end of the barrel, one of the radial ribs 120a and/or 120b will contact the detent 132 and stop the plunger assembly 102 from being pulled further from barrel 110. Each lengthwise rib 116a, 116b, or 116c can have an indention 118a, 118b, or 118c formed within the lengthwise ribs 116a, 116b, and/or 116c. The plunger assembly 102 can rotate within the barrel 110. To allow the lengthwise ribs 116a, 116b, and/or 116c to rotate, the indention 118a, 118b, or 118c allows the detent 132 to pass by the lengthwise rib 116a, 116b, or 116c. In other positions, the detent 132 rides within the channel for between two of the lengthwise ribs 116a, 116b, and/or 116c. Thus, once a dosage is set, that dosage is maintained until the user sets the syringe 100 for another dosage.

The syringe 100 can also include a force producing element 114. In embodiments, the force producing element 114 produces a force that extracts the plunger assembly 102 from the barrel 110. Thus, the plunger assembly 102 can be manually pushed into the barrel 110, and the force producing element 114 can push the plunger assembly 102 from the barrel 110. The force producing element 114, in embodiments, is a coil spring. However, the force producing element 114 can be a leaf spring, a hydraulic system, or other device that can produce a force as described herein. The force producing element 114 can be made from any semi-rigid material that has good tensile strength and will compress and decompress, for example, a metal.

In embodiments, the medication delivery system 100 further includes a window 128 formed into the barrel 110. The window 128 can be a clear or transparent section of the barrel 110 that provides a view to the shaft 106 of the plunger assembly 102. The barrel 110 may be painted or coated and the painting or coating may be missing from the window 128. In other embodiments, the barrel 110 is formed from a first material that is non-transparent and the window 128 is formed from a second transparent material. The barrel 110 may also be formed completely from a clear material, and the window 128 is shown by one or more markings.

The window 128 allows a user to see indicia 144 shown on the shaft 106 of the plunger assembly 102. As shown in FIGS. 3A-3D, the shaft 106 has four sections formed by pairs of the lengthwise ribs 116a, 116b, and/or 116c. The shaft 106 can have more or fewer sections than those shown. Indicia 144 are marked in a section of the shaft 106 between two lengthwise ribs 116a, 116b, and/or 116c. A radial rib 120 is formed between each of the pairs of the lengthwise ribs 116a, 116b, and/or 116c. The radial rib 120 is located at a predetermined distance along the shaft 106 such that the syringe will deliver the dosage indicated by the indicia 144 when that section of the shaft 106 is selected.

Figure 3D:
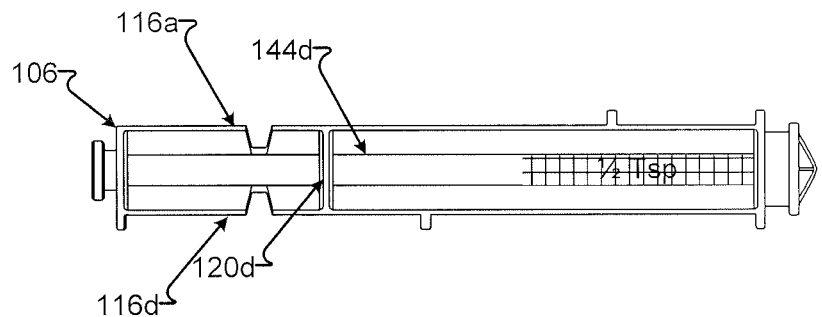
FIGS. 3A-D are two-dimensional views of embodiments of a shaft in a mediation delivery system.
Figure 3C:
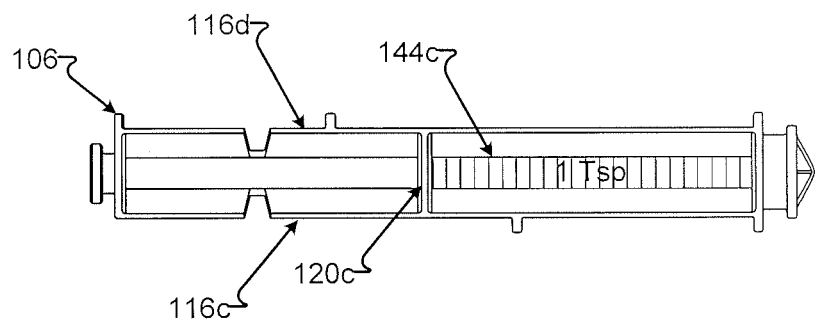
Figure 3B:
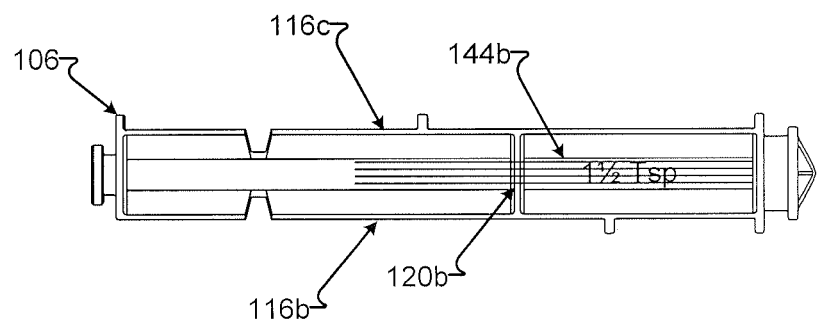
Figure 3A:
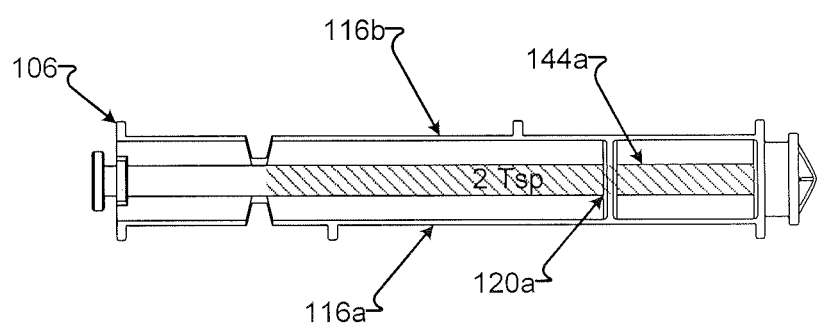

The indicia 144 can be one or more markings describing the predetermined volume that medication delivery system 100 will siphon when the plunger assembly 102 is pulled from the barrel 110. The indicia may be a word or measure, for example, "1 Tsp" as shown in FIG. 3B. The indicia 144 may also be a bar or other visual marking indicative of the predetermined volume. For example, one bar may be longer than another bar, as shown in FIGS. 3A-3D, to indicate that the volume is greater. In other embodiments, the indicia are color coded. For example, bar 144a is green, bar 144b is blue, bar 144c is red, and bar 144d is yellow. The colors can be part of a marking system as known in the industry. Each color can represent a predetermined dosage, e.g., green may represent a volume of 2 teaspoons or a color that is red may represent a volume of 1 teaspoon.

Figure 4A:
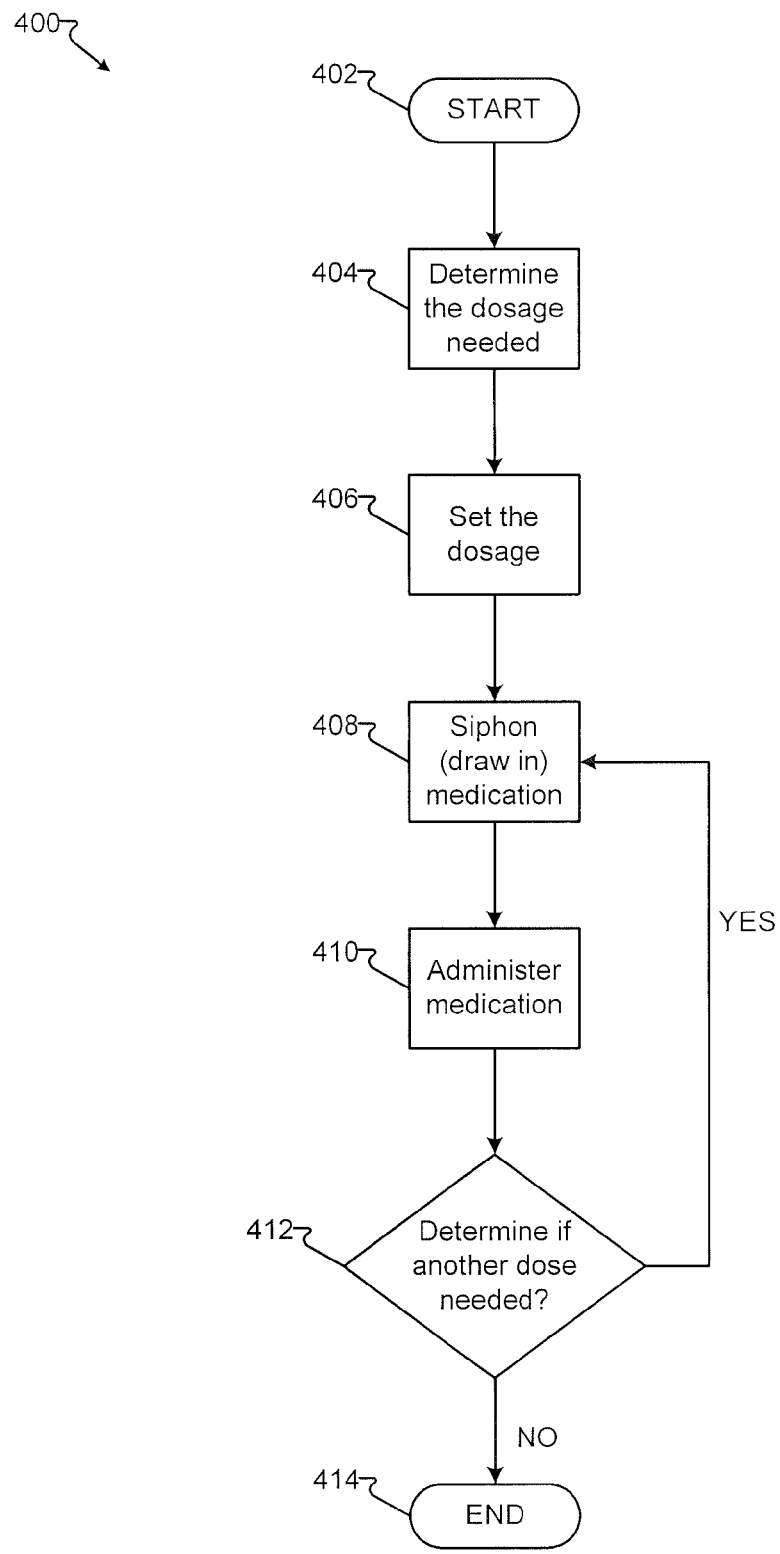
FIG. 4A is a flow diagram of an embodiment of a method for administering medication with a mediation delivery system.
Figures 4B, 4C:
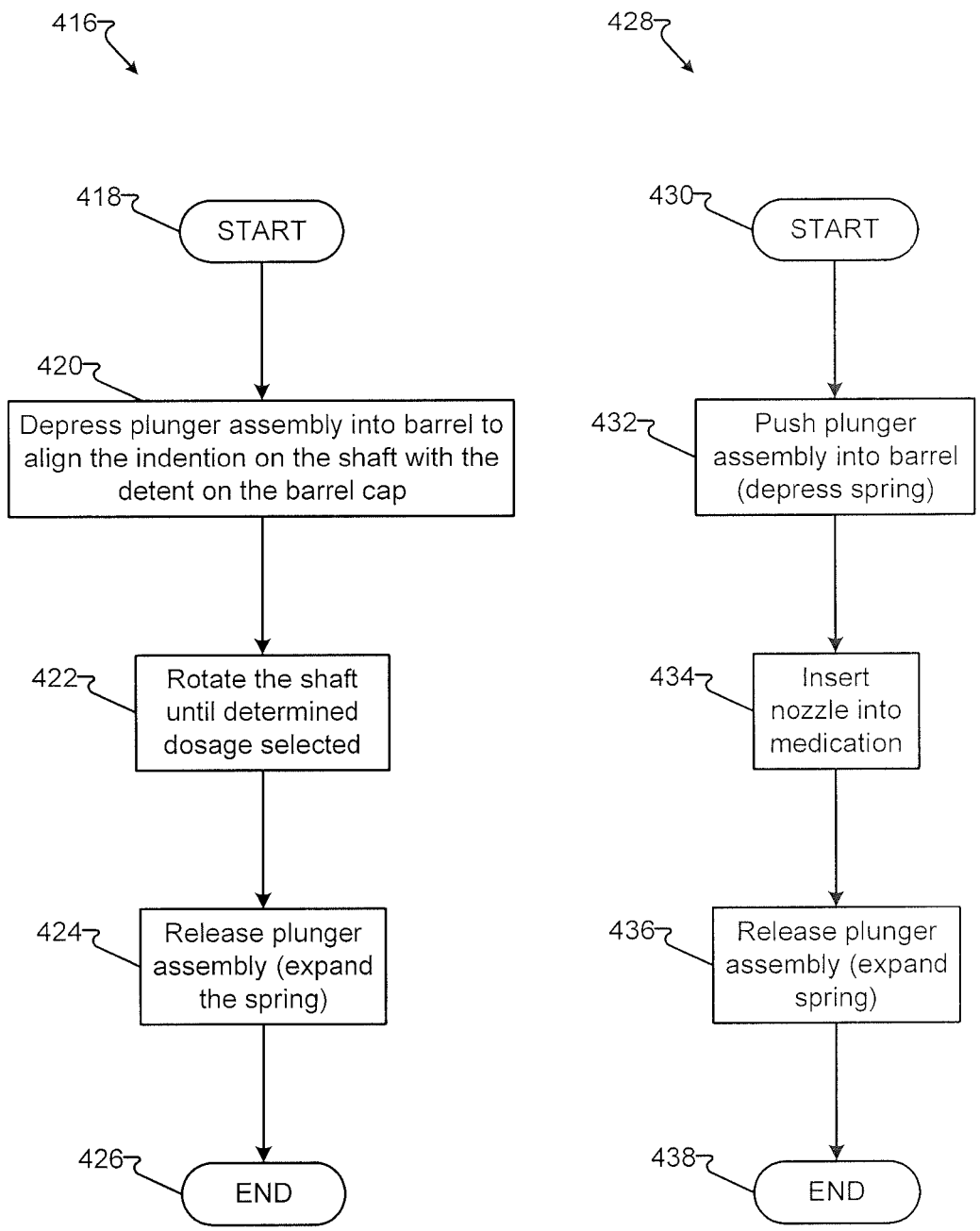
FIG. 4B is a flow diagram of an embodiment of a method for selecting a dosage with a mediation delivery system.
FIG. 4C is a flow diagram of an embodiment of a method for siphoning medication with a mediation delivery system.

A method 400 for administering a dosage of medicine with the medication delivery system 100 is shown in FIGS. 4A-4C. The method 400 will be explained in conjunction with FIGS. 1-3D. Generally, the method begins with a start operation 402 and terminates with an end operation 414. A user determines the dosage needed in step 404. The user can read the instructions on the label of the medication. The instructions may be presented by a doctor if the medication is prescription medication or by a company if the medication is over-the-counter. In embodiments, the instructions include a color-coded amount on the label. For example, green indicia may represent a volume of 2 teaspoons or red indicia may represent a volume of 1 teaspoon.

A user sets the dosage in step 406. The user can set the dosage by adjusting the syringe 100 to the proper dosage. For example, the user adjusts the position of the plunger assembly 102 within the barrel assembly 108 until the determined dosage is selected. An embodiment of a method 416 to select a dosage is shown in FIG. 4B.

Medication is siphoned into the medication delivery system 100 in step 408. The user can insert the nozzle 126 of the medication delivery system 100 into a receptacle holding a fluid medication. The user may then pull the plunger assembly 108 from the barrel 110 to draw the fluid into the barrel 110. In embodiments, the movement of the plunger assembly 108 being extracted from the barrel 110 creates a vacuum that draws the fluid into the barrel 110. A method 428 for siphoning medication is shown in FIG. 4C.

The user can administer medication in step 410. The user can insert the nozzle 126 into the mouth of the patient (the user and patient may be the same person). The user can then depress the plunger assembly 102 into the barrel 110. The plunger 104 may push the medication from the barrel 110 through the orifice in the nozzle 126 and into the patient's mouth. The act of depressing the plunger assembly 102 can compress the force producing assembly 114 (e.g., compress the coil spring).

A user may need to deliver another dose of medication to either another patient or to the same patient. The user may then determine if another dose is needed in step 412. If another dose of medication is needed, the method 400 flows YES to repeat steps 408 and 410. In embodiments, the user need not determine or set another dosage. With the medication delivery system 100 already set to provide a determined dose, the user need only siphon the medication again. The user siphons the substantially similar amount of medication. In other embodiments, the user may need to determine a new dose and repeats steps 404 through 410. If the user does not need to administer another dose, the method flows NO to end 414.

Figure 2E:
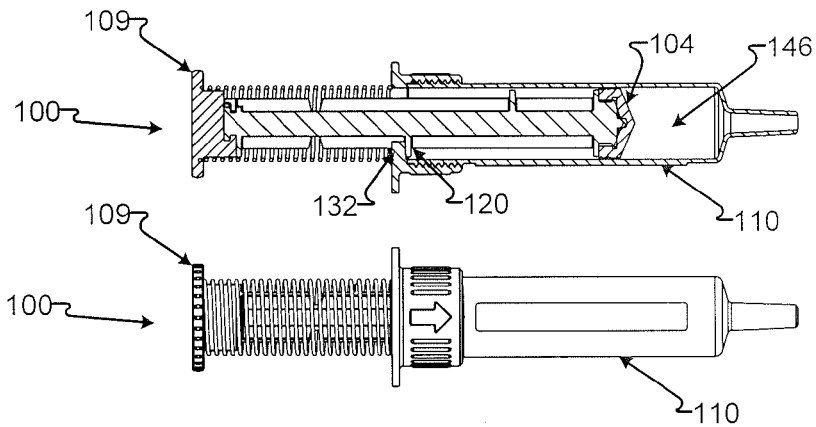
FIG. 2A-E are two-dimensional and cut-away views of embodiments of a mediation delivery system.
Figure 2D:
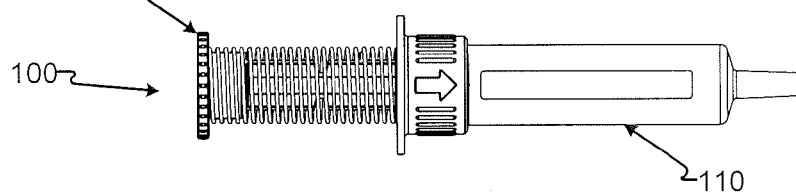
Figure 2C:
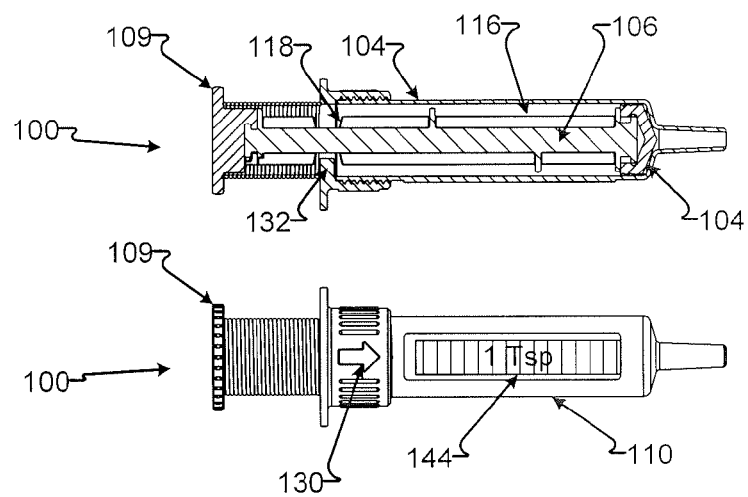
Figure 2B:
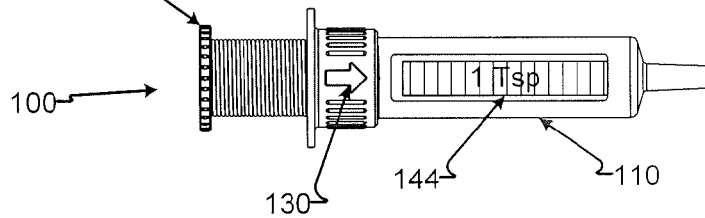
Figure 2A:
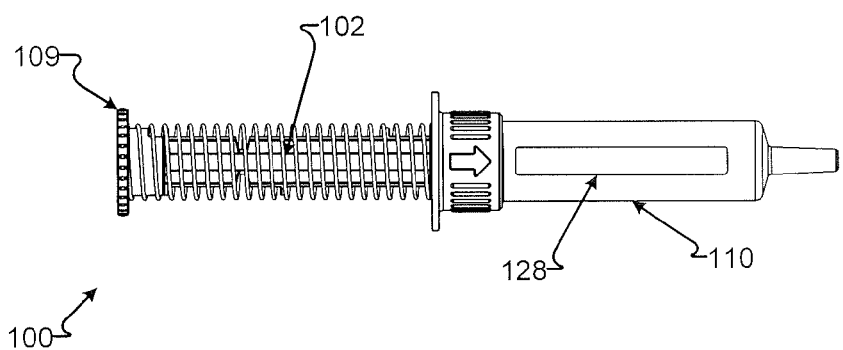

A method 416 for setting a dosage is shown in FIG. 4B. The method 416 will be explained in conjunction with FIGS. 1-3D. Generally, the method begins with a start operation 418 and terminates with an end operation 426. A syringe 100 can be in a first "neutral position" as shown in FIG. 2A. A user depresses the plunger assembly 102 into the barrel 110 in step 420. The user can depress the plunger assembly 102 by pushing the plunger cap 109 towards the barrel 110. The user stops depressing the plunger assembly 102 when the plunger assembly 102 is substantially oriented in the barrel 110 as shown in FIGS. 2B and 2C. Here, the shaft 106 is disposed within the barrel 110. The plunger 104 may be substantially near the distal end 132 of the barrel 110. More significantly, the indentions 118 in the lengthwise ribs 116 are substantially aligned with the detent 132 in the barrel cap 112 as shown in FIG. 2C.

The user rotates the plunger assembly 102 until the determined dosage is selected in step 422. While the plunger assembly is depressed as shown in FIGS. 2B and 2C, the user rotates the shaft 106 of the plunger assembly 102 within the barrel 110. The user can rotate the shaft 106 along the longitudinal axis of the shaft 106 by turning the plunger cap 109 either clockwise or counterclockwise in respect to the longitudinal axis. The lengthwise ribs 116 also rotate within the barrel 110. Further, the lengthwise ribs 116 pass by the detent 132 because the indentions 118 move past the detent 132. The user selects the appropriate dosage by viewing the dosages indicia 144 (as shown in FIGS. 3A-3D) through the window 128. For example, dosage indicia 144c are shown through the window 128 in FIG. 2B. The indicator 130 directs the user's attention to the window 128. If the indicia 144 for the predetermined dosage is shown in the window 128, the user has selected the predetermined dosage.

The user then releases the plunger assembly 102 in step 424. The user can stop depressing the plunger assembly 102 into the barrel 110. The force producing element 114 (e.g., the coil spring) produces a force on the plunger assembly 102. The force pushes the plunger assembly 102 from the barrel 110. In embodiments, the force is produced by the spring 114 attempting to return to a decompressed state. The force producing element 114 continues to push the plunger assembly 102 from the barrel 110 until the radial rib 120 associated with the set dosage contacts the detent 132, as shown in FIG. 2E. The position of the plunger assembly 102 in the barrel 110, as shown in FIGS. 2D and 2E, becomes the new "neutral position" for the medication delivery system 100. The neutral position is the position of the plunger assembly 102 within the barrel 110 without the user putting any force upon the medication delivery system 100. The volume 146 within the barrel 110 is the volume 146 associated with the determined dosage. The syringe 100 may thus siphon and administer the selected dosage every time the syringe 110 is used until the user selects a new dosage. Further, the user can use a single hand to depress the plunger assembly 102 to siphon the medication, allowing the force producing element 114 to extract the plunger assembly 102 from the barrel 110. Thus, the syringe 100 is easier to use than a typical syringe. In alternative embodiments, the medication delivery system 100 does not include a force producing element 114, and the user must pull the plunger assembly 102 from the barrel.

A method 428 for siphoning the medication with the medication delivery system 100 is shown in FIG. 4C. The method 428 will be explained in conjunction with FIGS. 1-3D. Generally, the method begins with a start operation 430 and terminates with an end operation 438. The user pushes the plunger assembly 102 into the barrel 110 after selecting the dosage in step 432. The user can push the plunger cap 109 towards the barrel 110 to depress the plunger assembly 102. By depressing the plunger assembly 102, the user also compresses or loads the force producing element 114.

The user can insert the nozzle 126 of the medication delivery system 100 into the medication in step 434. The medication may be in a bottle or other receptacle. Thus, the nozzle 126 is either long enough to be submerged into the medication or the barrel 110 has a small enough outside diameter to be inserted through the orifice of the bottle. The user then releases plunger assembly 102 in step 436. The user can reduce the amount of force produced on the plunger assembly 102 allowing the force producing element 114 to push the plunger assembly 102 from the barrel 110. The plunger 104 contacts the inner walls of the barrel 110 and creates an airtight seal within the barrel 110. Moving the plunger assembly 102 from the barrel 110 creates an increased volume 146 within the barrel. The syringe 100 creates a decrease in pressure within the barrel 110. The decreased pressure or vacuum draws the medication from the bottle and into the barrel 110 until the volume 146 is filled with the medication.

Figure 5:
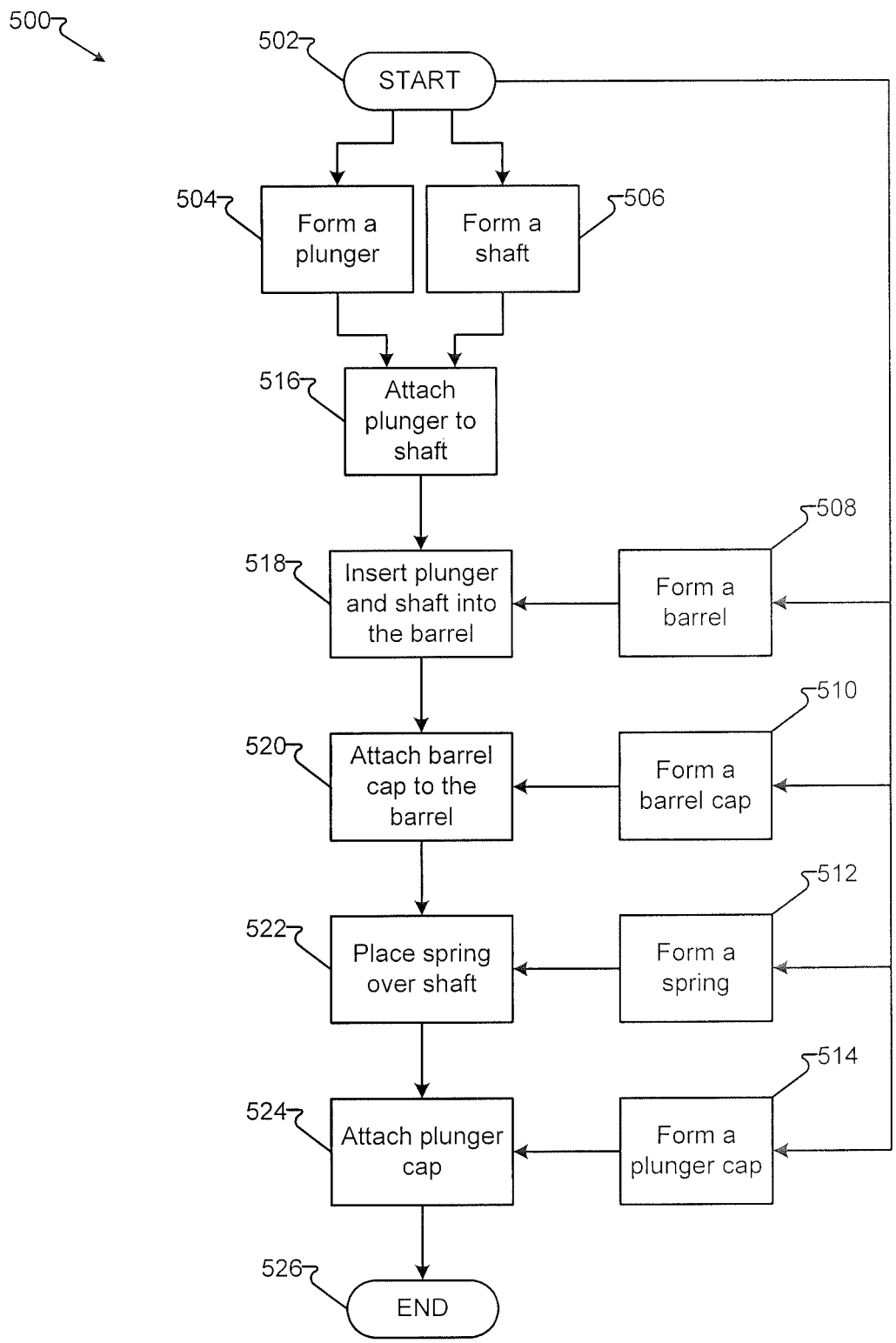
FIG. 5 is a flow diagram of an embodiment of a method for constructing a mediation delivery system.

A method 500 for assembly a medication delivery system 100 is shown in FIG. 5. The method 500 will be explained in conjunction with FIGS. 1-3D. Generally, the method begins with a start operation 502 and terminates with an end operation 526. A manufacturer forms a plunger 104 in step 504. Forming any component described herein can be a process to manufacture the component, such as injection molding, milling, or other process as known in the art. The manufacturer forms a shaft 106, with lengthwise ribs, radial ribs, indentions, etc. The manufacturer attaches the plunger 104 to the distal end 136 of the shaft 106 in step 516. In embodiments, the plunger 104 is formed around a tab or other protrusion formed in the distal end 136 of the shaft 106. In other embodiments, the plunger 104 is glued or adhered to the distal end 136 of the shaft 106. The plunger 104 may also be mechanically attached to the shaft.

The manufacturer can form a barrel 110, with a nozzle 126, a window 128, and optionally, threads 124 in step 508. The manufacturer inserts the plunger 104 and shaft 106 into the barrel 110 in step 518. The manufacturer forms a barrel cap 112 in step 510. The barrel cap 112 can then pass the barrel cap 140 over the shaft 106. Then, the barrel cap 112 can be attached to the barrel 110 in step 520. In embodiments, the barrel cap 112 can be threaded onto the threads 124 formed in the barrel 110. In other embodiments, the barrel cap 112 can be adhered or mechanically fastened to the barrel 110.

The manufacturer can form a spring or other force producing element 114 in step 512. The spring 114 can be placed over the shaft 106 in step 522. A plunger cap 109 can then be formed in step 514. The plunger cap 109 may then be attached to the shaft 106 to form the plunger assembly 102 in step 524. The plunger cap 109 may have a flange and an orifice accepting a protrusion formed in the proximal end 138 of the shaft 106. Thus, the plunger cap 109 can be mechanically fastened to the shaft 106. In other embodiments, the plunger cap 109 can be threaded onto the shaft or adhered to the shaft 106.

Figure 6C:
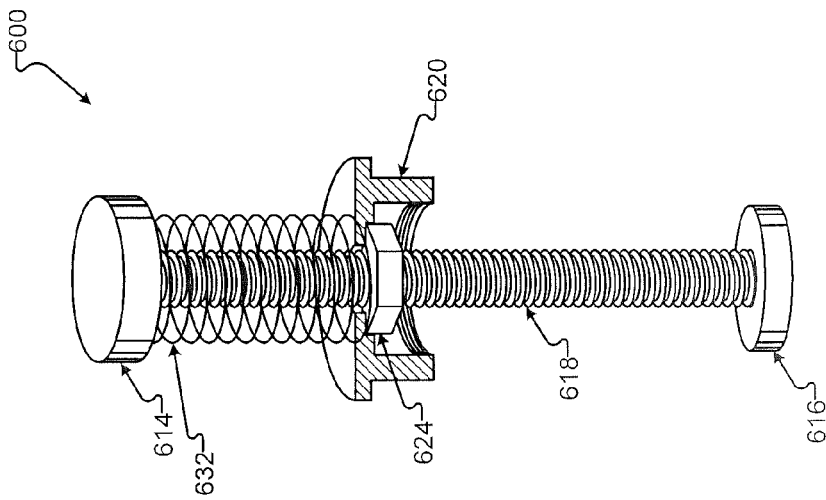
FIG. 6A-C are three-dimensional and partial cut-away views of alternative embodiments of a mediation delivery system.
Figure 6B:
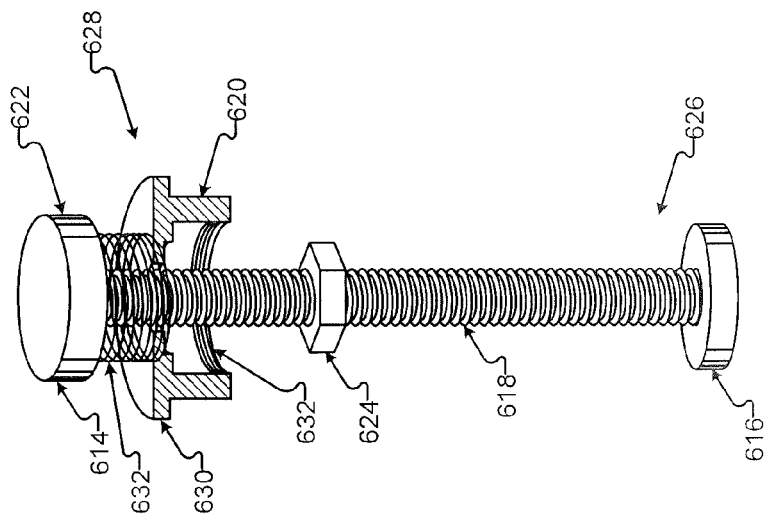
Figure 6A:
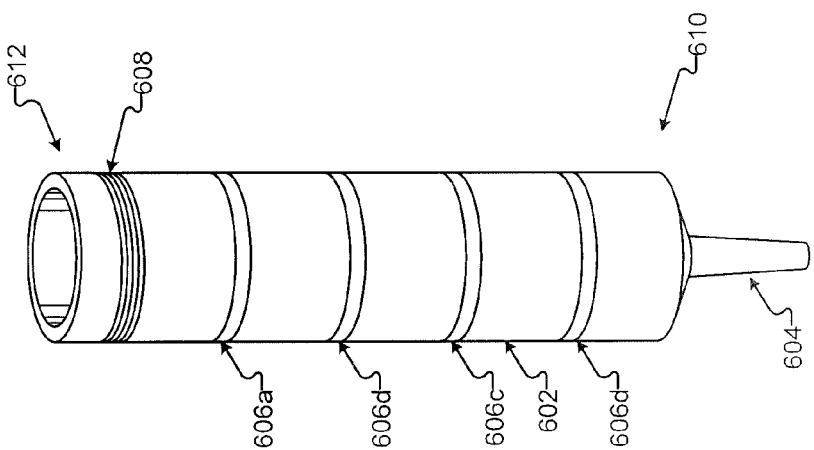

An alternative design for the medication delivery system 600 is shown in FIGS. 6A-6C. Here, the medication delivery system 600 includes a barrel 602. The barrel 602 can include a nozzle 604 at the distal end 610 of the barrel 602 and threads 608 in the proximal end 612 of the barrel 602. The barrel 602 may also include two or more indicia 606a, 606b, 606c, or 606d formed around the outside circumference of the barrel 602. The indicia 606a, 606b, 606c, or 606d may indicate the two or more dosages.

The medication delivery system 600 can also include a plunger assembly 614. The plunger assembly 614, similar to plunger assembly 102 (FIG. 1), can include a plunger 616, a shaft 618, and a plunger cap 622. The shaft 618 can be threaded to accept a nut 624. The nut 624 can be rotated about the longitudinal axis of the shaft 618 to move the nut 624 between the distal end 626 and the proximal end 628 of the shaft 618. The shall 618 may be disposed inside a barrel cap 630 that can be attached to the proximal end 612 of the barrel 602. Thus, the plunger assembly 614 is disposed within the barrel 602. A force producing element 632 can be disposed around the shaft 618 and between the barrel cap 630 and the plunger cap 622.

To select the determined dosage, the user depresses the plunger assembly 614 into the barrel 602 to expose the nut 624. The user then rotates the nut 624 along the shaft 618 until the plunger 616 is in line with one of the indicia 606. Thus, the barrel 602 may be formed of a clear material to shown the plunger 616 within the barrel 602. The user can release the plunger assembly 614 allowing the force producing element 632 to extract the plunger assembly 614 from the barrel 602. The force producing element 632 continues to push the plunger assembly 614 from the barrel 602 until the nut 624 contacts the inside surface of the barrel cap 620.

Figure 7C:
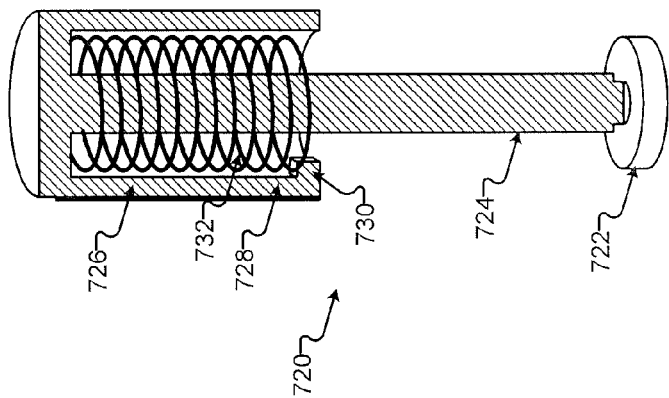
FIG. 7A-C are three-dimensional and partial cut-away views of other alternative embodiments of a mediation delivery system.
Figure 7B:
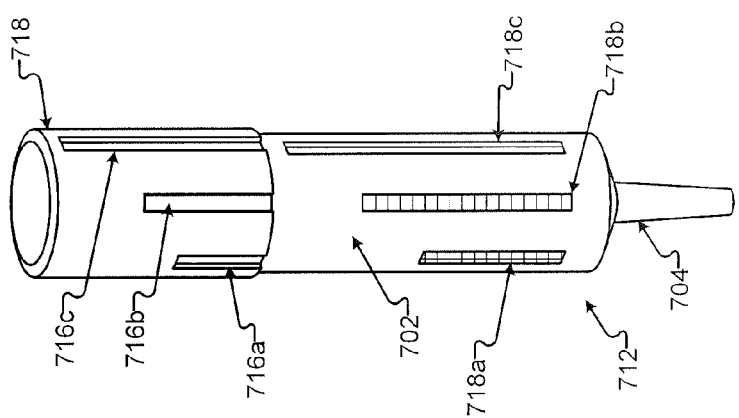
Figure 7A:
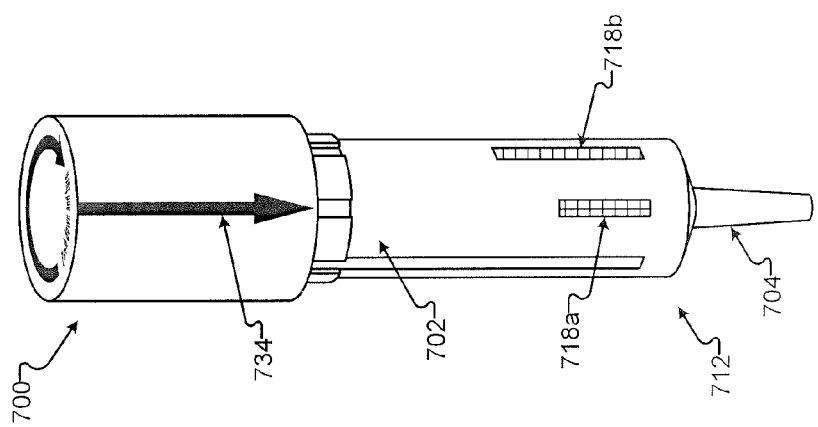

Another alternative design for the medication delivery system 700 is shown in FIGS. 7A-7C. Here, the medication delivery system 700 includes a barrel 702. The barrel 702 can include a nozzle 704 at the distal end 712 of the barrel 702 and two or more indentions 716a, 716b, or 716c formed in the proximal end 718 of the barrel 702. The barrel 702 may also include two or more indicia 718a, 718b, or 718c formed around the outside of the barrel 702 and inline or parallel with indentions 716a, 716b, or 716c. The indicia 718a, 718b, or 718c may indicate the two or more dosages.

The medication delivery system 700 can also include a plunger assembly 720. The plunger assembly 720, similar to plunger assembly 102 (FIG. 1), can include a plunger 722, a shaft 724, and a plunger cap 726. The shaft 724 may be disposed inside the barrel 702. The plunger cap 726 may be formed with an outside wall 728 such that the outside wall 728 is formed circumferentially around the outside of the proximal end 718 of the barrel 702. A detent 730 is formed at a predetermined location on the inside of the outside wall 728. The detent 730 is disposed in one of the indentions 716a, 716b, or 716c. A force producing element 732 can be disposed around the shaft 718 and inside the plunger cap 726.

To select the determined dosage, the user depresses the plunger assembly 720 into the barrel 702 to release the detent 730 from one of the indentions 716a, 716b, or 716c. The user then rotates the plunger assembly 720 until the indicator 734 is in line with one of the dosage indicia 718a, 718b, or 718c. The user can release the plunger assembly 720 allowing the force producing element 732 to extract the plunger assembly 720 from the barrel 702. The force producing element 732 continues to push the plunger assembly 714 from the barrel 702 until the detent 730 contacts the proximal end of the selected indention 716a, 716b, or 716c, shown in FIG. 7B.

In further embodiments, a needle may be disposed at the end of or instead of a nozzle 154. Further, the dosage may be selected by a doctor and set permanently so the same dosage would be given each time. This embodiment would prevent the user selecting the incorrect dosage. For example, the doctor or pharmacist would select the dosage by inserting the plunger assembly 102 into the barrel 110 with the detent 132 between the correct pair of lengthwise ribs 116. Then, the doctor or pharmacist can complete the construction of the plunger assembly 102 by attaching the force producing element 114 and plunger cap 109. The lengthwise ribs 116a, 116b, and/or 116c would not have an indention 118 that would allow the selection of a different dosage.

While various aspects of embodiments of the disclosure have been summarized above, the following detailed description illustrates exemplary embodiments in further detail to enable one of skill in the art to practice the disclosure. In the description, for the purposes of explanation, numerous specific details are set forth in order to provide a thorough understanding of the present disclosure. It will be apparent, however, to one skilled in the art that the present disclosure may be practiced without some of these specific details. Several embodiments of the disclosure are described, and while various features are ascribed to different embodiments, it should be appreciated that the features described with respect to one embodiment may be incorporated with another embodiment as well. By the same token, however, no single feature or features of any described embodiment should be considered essential to the disclosure, as other embodiments of the disclosure may omit such features. Specific details are given in the description to provide a thorough understanding of the embodiments. However, it will be understood by one of ordinary skill in the art that the embodiments may be practiced without these specific details.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be rearranged. A process is terminated when its operations are completed, but could have additional steps not included in the figure.

In light of the above description, a number of advantages of the present disclosure are readily apparent. For example, the syringe provides a simple way of selecting a dose of medication. Thus, the chance of selecting and administering the wrong dose is reduced. Further, the syringe will provide the same dosage repeatedly without the user having to measure a second or subsequent dose. Still further, with the force producing element, the user can use the syringe with one hand.

It will be apparent to those skilled in the art that substantial variations may be made in accordance with specific requirements. For example, different arrangements of components or materials might also be used. While the principles of the disclosure have been described above in connection with specific apparatuses and methods, it is to be clearly understood that this description is made only by way of example and not as limitation on the scope of the disclosure.

What is claimed is:

1. A method for selecting a dose of medication, the method comprising:
   compressing a plunger assembly into a barrel assembly, wherein the plunger assembly includes a shaft having a distal end and a proximal end;
   rotating the plunger assembly within the barrel assembly to select a dosage by viewing visual indicia indicative of the dosage;
   inserting the barrel assembly into a fluid;
   releasing the plunger assembly such that a force producing element produces a force on the plunger assembly;
   the force producing element extracting the plunger assembly from the barrel assembly until a radial rib contacts a detent on a barrel cap assembly, wherein the radial rib is disposed between two or more lengthwise ribs; wherein the radial rib is disposed in at least one portion of a circumference of the shaft, but not extending along a full circumference of the shaft; and
   wherein the radial rib is disposed lengthwise on the shaft between the distal end and the proximal end of the shaft to provide a predetermined volume of the fluid in the barrel assembly when the radial rib contacts the barrel cap assembly; and
   siphoning the fluid into the barrel assembly as the plunger assembly is extracted.

2. The method as defined in claim 1, wherein compressing the plunger assembly includes pushing a plunger cap toward the barrel assembly to compress the force producing element.

3. The method as defined in claim 1, wherein compressing the plunger assembly includes compressing the plunger assembly into the barrel assembly until an indention, formed within the two or more lengthwise ribs, is in line with the detent.

4. The method as defined in claim 1, wherein rotating the plunger assembly includes rotating the two or more lengthwise ribs within the barrel assembly by rotating the detent by at least one indention formed within the two or more lengthwise ribs.

* * * * *